United States Patent
Yu

(10) Patent No.: US 8,828,672 B2
(45) Date of Patent: Sep. 9, 2014

(54) PARP SUBSTRATES AND BIOMARKERS

(71) Applicant: Board of Regents, The University of Texas System, Dallas, TX (US)

(72) Inventor: Yonghao Yu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/874,453

(22) Filed: Apr. 30, 2013

(65) Prior Publication Data

US 2014/0170643 A1     Jun. 19, 2014

Related U.S. Application Data

(60) Provisional application No. 61/640,340, filed on Apr. 30, 2012.

(51) Int. Cl.
*G01N 33/53* (2006.01)
*C07K 16/40* (2006.01)
*G01N 33/68* (2006.01)

(52) U.S. Cl.
CPC ............ *C07K 16/40* (2013.01); *G01N 2440/40* (2013.01); *G01N 33/68* (2013.01)
USPC ............................................. 435/7.1; 435/7.2

(58) Field of Classification Search
None
See application file for complete search history.

(56) References Cited

PUBLICATIONS

Tempera et al. Journal of Virology 2010 vol. 84, p. 4988-4997.*

* cited by examiner

*Primary Examiner* — Jacob Cheu
(74) *Attorney, Agent, or Firm* — Richard Aron Osman

(57) ABSTRACT

PARylated proteins are enriched by treating cell lysates comprising PARylated proteins and DNA/RNA with an endonuclease that cleaves the DNA/RNA but not the PAR; and separating the PARylated proteins from the cleaved DNA/RNA. PARylation sites are labeled by eluting PARylated proteins from a PAR-affinity substrate with a nucleophilic amine exchange reactant, wherein the reactant labels PARylation sites of the proteins. Specific binding agents are identified by screening compounds for specific binding to a PARylated protein disclosed herein; and identifying one of the compounds as a specific binder of the protein. Antibodies which specifically bind PARylation sites are also disclosed.

18 Claims, No Drawings

PARP SUBSTRATES AND BIOMARKERS

CROSS-REFERENCE TO RELATED APPLICATION

This application claims priority to U.S. Ser. No. 61/640,340, filed Apr. 30, 2012.

INTRODUCTION

Poly-ADP-ribosylation (PARylation) is a protein post-translational modification that is catalyzed by a family of enzymes known as poly-ADP-ribose polymerases (PARPs). PARP1 is activated as a result of sensing nicked DNA and PARP1-mediated protein PARylation plays a pivotal role in DNA repair mechanisms.

Cancer cells that carry BRCA1/2 mutations are reliant on PARP1 for genome integrity and have been shown to be exquisitely sensitive to PARP1 inhibition. PARP inhibitors are also considered as a potential treatment for stroke, myocardial infarction as well as various long-term neurodegenerative diseases. Recent late-stage clinical trials of PARP1 inhibitors in treating cancer patients, however, yielded disappointing results, i.e. the progression-free survival benefit observed previously did not translate into an overall survival benefit. These results indicate that a better strategy of patient stratification will be critical for utilization of PARP inhibitors as a potential cancer therapy. Importantly, despite decades of intensive research, genuine substrates of PARP1 and their endogenous sites of modification remain poorly defined, which has hampered the development of methods for determining PARP activity in a cell.

We developed and disclose an integrated approach for a site-specific characterization of the mammalian PARylated proteome and report here identification of 1048 unambiguously assigned PARylation sites on 334 proteins. Many proteins in the canonical base excision repair mechanism were found to be PARylated. In addition, PARylated proteins were involved in many other nuclear functions including chromosome organization, RNA splicing and transcription regulation. We performed quantitative mass spectrometric analysis and showed that the majority of these PARylation events were sensitive to the treatment of a specific PARP1 inhibitor, olaparib.

SUMMARY OF THE INVENTION

The invention provides methods and compositions for enriching for PARylated proteins and/or labeling their PARylation sites, biomarkers comprising the labeled PARylation sites and/or PARylated proteins identified herein, and antibodies specific for a PARylated protein or biomarker as disclosed herein.

In an aspect the method provides a method for detecting sites of ADP-ribosylation comprising steps: (a) enriching for PARylated proteins comprising treating cell lysates comprising PARylated proteins and DNA/RNA with an endonuclease that cleaves the DNA/RNA but not the PAR; and separating the PARylated proteins from the cleaved DNA/RNA; and/or (b) labeling PARylation sites comprising eluting PARylated proteins from a PAR-affinity substrate with a nucleophilic amine exchange reactant, wherein the reactant labels PARylation sites of the proteins.

In embodiments the method:
further comprising: repeating the steps in the presence and absence of an inhibitor of ADP-riboylation, and detecting changes in protein ADP-ribosylation as a result of the inhibitor;
further comprising stable isotope labeling by amino acids in cell culture (SILAC); and/or
wherein a PARP1 Asp/Glu-ADP-ribosylation site is labeled and detected, the site selected from: Glu75, Asp80, Glu89, Glu115, Glu129, Asp154, Glu167, Glu174, Asp190, Glu211, Asp216, Glu217, Glu275, Asp306, Asp313, Glu359, Glu447, Asp456, Glu470, Glu483, Glu512, Glu513, Glu539, Asp560, Glu575, Asp576, Glu641, Asp643, Asp647 and Glu649.

In an aspect the invention provides stable isotope labeling by amino acids in cell culture (SILAC) method for detecting changes in protein ADP-ribosylation: (a) contacting one of two cell cultures with a stimulus effecting differential PARylation of the cultures, wherein one of the cultures is labeled with an amino acid comprising a stable, heavy stable isotope; (b) forming a mixture of the cultures or portions thereof; (c) isolating from the mixture PARylated proteins; and (d) quantitatively determining differential protein PARylation of the cultures based on differential isotope labeling of the cultures.

In an aspect the invention provides an isolated PARP1 peptide comprising only one modified Asp/Glu selected from Glu75, Asp80, Glu89, Glu115, Glu129, Asp154, Glu167, Glu174, Asp190, Glu211, Asp216, Glu217, Glu275, Asp306, Asp313, Glu359, Glu447, Asp456, Glu470, Glu483, Glu512, Glu513, Glu539, Asp560, Glu575, Asp576, Glu641, Asp643, Asp647, and Glu649.

In embodiments:
the ASP/Glu is modified with ADP-ribosylation or amine substitution, such as n-hydroxyl-asparagine or n-hydroxyl-glutamine, and/or
the peptide comprises, consists of, or consists essentially of 8-18 contiguous PARP1 residues including and/or centered by the Asp/Glu, wherein essentially means that the essential functionality (e.g. specific immunogenicity or antigenicity) is contributed by the recited residues.

In an aspect the invention provides antibodies specific to the disclosed peptides.

The invention provides all combinations of recited embodiments as if each combination had been separately recited.

DETAILED DESCRIPTION OF PARTICULAR EMBODIMENTS

The invention provides methods and compositions for enriching for PARylated proteins and/or labeling their PARylation sites.

In an aspect the method provides a method for detecting sites of ADP-ribosylation comprising steps: (a) enriching for PARylated proteins comprising treating cell lysates comprising PARylated proteins and DNA/RNA with an endonuclease that cleaves the DNA/RNA but not the PAR; and separating the PARylated proteins from the cleaved DNA/RNA; and/or (b) labeling PARylation sites comprising eluting PARylated proteins from a PAR-affinity substrate with a nucleophilic amine exchange reactant, wherein the reactant labels PARylation sites of the proteins.

In particular embodiments the cells are lysed with a surfactant, such as SDS, that permeablizes membranes of the cell, and preferably inactivates and/or denatures enzymes of the cell, particularly PARG, and preferably without precipitating the lysates, proteins and/or nucleic acids of the cell.

In alternative embodiments, the lysis medium may provide a PARG inhibitor, particular wherein the surfactant is a mild detergent that does not sufficiently inactivate PARG. Alternative lysis methods and reagents may be uses, such as methylchloroform provided the method preserves PARylation sites.

Preferred endonucleases are promiscuous, and degrade both DNA and RNA, preferably including single-stranded, double-stranded, circular or supercoiled, and preferably showing no base preference, wherein upon digestion, all free nucleic acids present in solution are reduced to short 5'-monophosphate-terminated oligonucleotides, generally 3-8 bases. A preferred example is an endonuclease from *Serratia marcescens*—a commercially available, genetically engineered for is Benzonase™, Novagen).

In alternative embodiments, the separating is done by any means that effectively separates the PARylated proteins from the cleaved DNA/RNA, and may include size filtration, dialysis, size or affinity chromatography, gel-based methods, centrifugation, etc.

The affinity substrate preferentially binds PAR over forms of DNA and RNA, and suitable examples include boronate substrate, PAR-specific antibody substrate, etc. The substrate is conveniently a solid phase, such as a resin bead based column, flow cell, surface, etc. In particular, embodiments, the method comprises the antecedent step of binding the proteins to the substrate, and optionally, a method of enriching for PARylated proteins as described herein.

In particular embodiments a reaction of the reactant and an ester of a Glu/Asp residue of the proteins generates an amide derivative of the Glu/Asp. Hydroxylamine is a preferred reactant, but can be substituted with alternative nucleophilic amine exchange reactants (hydrazine, etc.) compatible with the method.

In particular embodiments, the method further comprises the subsequent step of detecting the now-labeled PARylation sites (e.g. by mass spectroscopy).

In another aspect the invention provides isolated biomarkers comprising the labeled PARylation sites and/or PARylated proteins identified herein. The biomarkers are isolated from their native context to provide specificity. Generally these biomarkers comprise a peptide of 1 to 5, 10, 20, 50 or 100 residues flanking, on one or both sides, the PARylation site, for example 2, 3, 4, 5, 6, or 7 flanking residues, independently on one or both sides.

In another aspect the invention provides pharmaceutical screening methods comprising: (a) screening compounds for specific binding to a PARylated protein or PARylated peptide biomarker disclosed herein; and (b) identifying one of the compounds as a specific binder of the protein.

In various embodiments the compounds may be small molecules of chemical library, particular a library enriched for biologically-active compounds, putative or candidate inhibitors of PAR-ylation, antibodies (including component pieces thereof), etc.

In another aspect the invention provides antibodies specific for a PARylated protein or biomarker as disclosed herein.

In preferred embodiments, the antibodies specifically-recognize a disclosed PARylation site. The antibodies may be generated from and bind specifically to the unmodified PARylation sites, or the labeled (e.g. amide-labeled) sites. Such antibodies may be used, for example, to measure the sensitivities of different PARylation sites to different PARP inhibitors. The antibodies are made with routine methods using the disclosed PARylation-site containing peptides (PARylated or labeled) as immunogens and antigens, such as is routinely done with other tagged peptides, e.g. ubiquitinated peptides.

In particular embodiments, the invention provides an array of subject antibodies to facilitate high-throughput and/or parallel assays. The invention provides these arrays in all subcombinations and subsets of the antibodies, as if each had been laboriously individually set forth. For example, the antibodies may be grouped or arrayed in sets of antibodies with respective specificity for biomarkers grouped in consecutive or arbitrary groups of 2, 5, 10, 25, 50 or 100 biomarkers or proteins.

The invention also provides methods and biomarkers for initiating a treatment for a subject with a neoplastic disease, such as a cancer, which exhibits an elevated level of protein PARylation compared to a reference, for example, normal cells isolated from the same patient. The same approach can also be applied in the subject with cardiovascular and neurodegenerative diseases who is under the treatment of a PARP1 inhibitor.

There are no previously known in vivo PARylation sites on proteins that can serve as markers for activation of PARP, which in turn, has made patient stratification exceedingly difficult for PARP inhibitor-based cancer therapies. The method we developed allows for a quantitative survey of the PARylated proteome, which provides an excellent biomarker for inhibitor efficacy evaluation and patient-response prediction. Current PARP inhibitors in clinical trials include: Iniparib (Sanofi), Olaparib (AstraZeneca), Rucaparib (Pfizer), Veliparib (Abbott), CEP-9722 (Cephalon), MK4827 (Merck), BMN-673 (Biomarin), among others.

There are no prior useful methods for measuring the sites and levels of endogenous protein PARylation. By measuring the site-specific levels of protein PARylation, we determine the activities of PARP in a cell. Applications of our method include (1) comparing the PARP activities in samples from cancer patients for stratification, (2) and measuring the PARP activities in cells or tissue after a PARP inhibitor has been administered, for evaluation of the efficacy of this inhibitor. (3) the identified PARP substrates or antibodies thereto, or arrays of such substrates or antibodies can be used to assay PAPP activities on a large scale or for high-throughput screening of potential PARP inhibitors.

EXAMPLES

Site-Specific Characterization of the Aspartic Acid/Glutamic Acid-ADP-Ribosylated Proteome In this example we characterized the human Asp/Glu-ADP-ribosylated proteome and identified 1048 unambiguously assigned Asp/Glu-ADP-ribosylation sites on 334 proteins that are involved in a wide array of nuclear functions. We identified many novel PARP downstream targets whose ADP-ribosylation was sensitive to the treatment of PARP inhibitors. Finally we confirmed that Iniparib had a negligible effect on PARP activity in intact cells.

Poly-ADP-ribosylation (PARylation) is a protein post-translational modification (PTM) that was first documented more than four decades ago[1]. It is composed of a linear and/or branched repeats of ADP-ribose, whose length can reach up to 200 units. PARylation often results in a dramatic change in the electrostatic property of the acceptor protein (each ADP-ribose contains two negative charges)[2]. PAR may also act as a scaffold for recruiting other proteins to modulate the function of the acceptor protein[3]. PARylation is synthesized by a class of enzymes called poly-ADP-ribose polymerases (PARPs, 17 members identified so far[4]). In particular, PARP1 is a nuclear protein that is activated as a result of sensing DNA strand breaks[5]. In response to genotoxic stress, PARP1 is rapidly recruited to nicked DNA and its catalytic activity increases by up to 500-fold, resulting in the synthesis of a large number of PARylated proteins and initiation of the DNA damage repair mechanisms[6].

Cancer cells with defects in double-strand break (DSB) repair, such as the BRCA1/2-mutated cells, are reliant on PARP1 activity for genome integrity, and undergo unsustainable genetic damage upon PARP1 inhibition[7]. However, recent late-stage clinical trials revealed the disappointing results that there was no overall survival benefit of PARP inhibitors in treating triple-negative breast cancer patients[8]. These setbacks underscore that the challenge remains to understand the exact role PARP plays in oncogenesis and tumor maintenance.

Affinity purification experiments using protein domains or antibodies that recognize PAR have been used to capture PARylated proteins for their subsequent identification[9,10]. However, pinpointing the site of ADP-ribosylation turns out to be a critical challenge for mass spectrometry. Protein PARylation is a heterogeneous modification, which precludes the usage of conventional database search approaches for spectrum interpretation. In addition, its pyrophosphate bond, adenine moiety and side-chain linkage are labile during CID (collision-induced dissociation) experiments, yielding neutral-loss fragments instead of sequence-specific ions for site-localization[11,12]. As a result, PARylation sites have so far been determined for only a few proteins, including histone H1, histone H2B, seminal ribonuclease, p53 and PARP, etc[13], even though a number of amino acids are known to be ADP-ribosylated, including aspartic acid, glutamic acid, lysine, arginine, cysteine and asparagine residues[14].

We sought to develop an approach towards a global characterization of Asp/Glu-ADP-ribosylation. During the initial characterization of the cellular response to genotoxic stress, we observed increased PARylation in HCT116 cells after MNNG (1-methyl-2-nitro-1-nitrosoguanidine, a DNA-alkylating agent) treatment. However, the level of increase was marginal even though PARP1 is dramatically activated in these conditions[6]. The major cellular enzymatic activity for degrading PAR is from poly-ADP-ribose glycohydrolase (PARG)[2]. To facilitate the downstream isolation and characterization of these low abundance PARylated proteins, we generated PARG-depleted cells, in which we observed a pronounced accumulation of PAR-modified proteins after MNNG or $H_2O_2$ treatment Importantly, the increased PARylation was mediated by PARP because it was blocked by pretreatment of the cells with a PARP inhibitor, Olaparib.

We used boronate affinity chromatography to isolate ADP-ribosylated peptides. The mechanism of enrichment is based on the formation of ester bonds between boron and a 1,2-cis-diol moiety within ADP-ribose[15]. We eluted the ADP-ribosylated peptides using $NH_2OH$ treatment. The ester bond between the first ADP-ribose unit of PAR and the side chain carboxyl group of an Asp/Glu residue is susceptible to $NH_2OH$ attack[16,17]. However, instead of converting an ADP-ribosylated Asp/Glu back to its unmodified form, which results in loss of the site information, the reaction with $NH_2OH$ generates a hydroxamic acid derivative of Asp/Glu with an addition of 15.0109 Da, an increment that can be readily distinguished by mass spectrometry. Notably, transformation of a heterogeneously modified (Poly-ADP-ribosylated) amino acid into a residue with a fixed mass tag greatly facilitates the concurrent identification and site-determination of Asp/Glu-ADP-ribosylated proteins. We confirmed that $NH_2OH$ did not react non-specifically with free Asp and Glu residues.

In two experiments, we stimulated PARG-depleted HCT116 cells with 0.2 mM or 2 mM $H_2O_2$, from which we identified a total of 883 Asp/Glu-ADP-ribosylated peptides from 219 proteins, and 1129 Asp/Glu-ADP-ribosylated peptides from 154 proteins, respectively. There was a substantial overlap in the identified proteins, with 102 of them commonly found in both experiments. We also confirmed that combination of PARG-depletion and short-term $H_2O_2$ treatment did not induce a general apoptosis response. We performed Gene Ontology analysis and found that the modified proteins were enriched for the base excision repair pathway ($P=3.45\times10^{-7}$), spliceosome ($P=7.96\times10^{-6}$), DNA replication ($P=2.15\times10^{-4}$) and cell cycle ($P=0.004$). In addition, many proteins involved in chromosome organization and epigenetic regulation were ADP-ribosylated, including members of the SMC proteins, and CTCF (supplementary text). We also applied the method to characterize the Asp/Glu-ADP-ribosylated proteome in response to MNNG treatment (supplementary text).

Fragmentation of $NH_2OH$-derivatized peptides yielded typical b- and y-series of ions, allowing facile localization of the ADP-ribosylation sites. It was previously shown that using a PARP1 mutant that catalyzed mono-(ADP-ribosylation), PARP1 auto-modification sites were mapped to Asp386, Glu487 and Glu490. However, mutation of these residues did not change the overall level of auto-PARylation of the full length protein, indicating that there were additional modification sites[13]. More recently, by using phosphodiesterase treatment in combination with $TiO_2$ enrichment, Chapman et al. was able to identify 12 ADP-ribosylation sites on PARP1, with most of them localized to Asp/Glu residues[18]. We found that, in vivo, PARP1 was automodified with a total of 37 unambiguously assigned Asp/Glu-ADP-ribosylation sites (supplementary text). Many of the PARP auto-modification sites and their flanking amino acid sequences are highly conserved evolutionally and thus are potentially functionally relevant. Mapping of the identified sites onto the structure of PARP1 favors the model that PARP1 might be automodified in trans[19] (supplementary text). We also verified several ADP-ribosylated proteins, including PCNA, DDX21 and GAR1, by using an immunoblotting assay. Finally, we mutated the identified sites on GAR1 and found the mutant to have a greatly reduced level of ADP-ribosylation.

We performed stable isotope labeling by amino acids in cell culture (SILAC) experiments and observed a dramatic change in the overall profile of protein ADP-ribosylation after Olaparib treatment, with the intensity of more than 81% of the modified peptides decreased by more than two-fold. We repeated the experiment using Lys and Arg double labeling and obtained a similar finding. Many Asp/Glu-ADP-ribosylation sites showed exquisite sensitivity to PARP inhibition. For example, the level of a PARP1 auto-modified peptide comprising E483 decreased by approximately 120-fold after Olaparib treatment. In another example, ADP-ribosylation of two evolutionarily conserved Glu residues on PCNA also dramatically decreased following PARP inhibition. ADP-ribosylation of two tankyrase substrates, CASC3 and BLZF1[20], however, showed little change after Olaparib treatment, in agreement with that Olaparib does not inhibit tankyrase[6].

We characterized the response of the Asp/Glu-ADP-ribosylated proteome to four additional PARP inhibitors, including A966492, AG14361, Iniparib and 3-aminobenzamide (3-AB) Immunoblotting experiments revealed that 1 µM A96692 or AG14361 treatment potently inhibited $H_2O_2$-induced PARP activation. Mass spectrometric analyses showed that the change in protein Asp/Glu-ADP-ribosylation upon the treatment of these two compounds correlated well with that of Olaparib. In contrast, even at 50 µM, Iniparib had little effect on $H_2O_2$-induced hyper-PARylation, an observation that agrees with two recent studies that challenged the status of Iniparib as a genuine PARP inhibitor[21,22]. Our mass spectrometric results further showed that, although a peptide from the RNA helicase DDX21 decreased by about 4-fold upon Iniparib (50 µM) treatment, most of the peptides we identified had a change in their ADP-ribosylation level of less than two fold, indicating that Iniparib has a negligible effect on PARP activity in intact cells (supplementary text).

We identified a total of 1048 unique, unambiguously localized Asp/Glu-ADP-ribosylation sites on 334 proteins. ADP-ribosylation predominantly occurred on Glu residues, representing 80.4% of the sites pinpointed. Examination of a six-amino-acid window adjacent to modified Glu residues revealed several consensus motifs (P<0.001), including PxE*, E*P, PxxE* and E*xxG, etc. ADP-ribosylated Glu residues also had a marked tendency to reside on protein surfaces (supplementary text). These results indicate that solvent-accessibility may be an important determinant for a residue to be modified.

In summary, we identified many novel ADP-ribosylated proteins that are involved in wide array of nuclear functions. We identified PARP downstream targets whose Asp/Glu-ADP-ribosylation was sensitive to the treatment of PARP inhibitors. We expect that these PARP targets will seed the discovery of mechanisms of how PARP regulates these important biological processes. Finally, we confirmed that Iniparib, a compound that is under clinical studies for treating various types of human cancer, failed to inhibit PARP in intact cells.

Materials and Methods

Cells and Reagents: HCT116 and HEK293T cells were purchased from ATCC and were maintained in Dulbecco's modified Eagle's medium (DMEM) supplemented with 10% fetal bovine serum. PARP inhibitors were purchased from Selleck. Anti-Poly-(ADP-ribose) Monoclonal Antibody was purchased from Trevigen (4335-MC-100). pCMV-Sport6-GAR1 and pCMV-Sport6-DDX21 were kind gifts from Dr. Lawrence Lum (UT Southwestern Medical Center). Anti-HA antibody was purchased from Cell Signaling Technology (CST #3724). Other chemicals and reagents were obtained from Sigma unless indicated otherwise.

SILAC cell culture: Cells (HCT116 shPARG) were grown in the SILAC media as described previously[23]. Both light and heavy DMEM were supplemented with 10% dialyzed FBS (Invitrogen). Where indicated, cells were pretreated with 1 µM Olaparib for 40 min and were stimulated with 2 mM $H_2O_2$ for 5 min. We performed two experiments using this experimental design with single labeling with Lys (sample digested with Lys-C) or double labeling with Lys and Arg (sample digested with trypsin). Each experiment was composed of two technical replicate analyses. The same experiment (Lys labeling only) was repeated for four other PARP inhibitors, including A966492 (1 µM), AG14361 (1 µM), Iniparib (50 µM) and 3-AB (50 µM).

Sample preparation for mass spectrometric analysis: Cells were lysed in SDS lysis buffer (1% SDS, 10 mM HEPES pH 7.0, 2 mM $MgCl_2$, 500 U Benzonase). Lysates were washed with SDS lysis buffer for three times using centricon ultrafiltration units (MWCO=10,000 Da, Millipore). Lysates were reduced by adding DTT to a final concentration of 3 mM, followed by incubation at room temperature for 20 min. Cysteines were alkylated by adding iodoacetamide to a final concentration of 50 mM, followed by incubation in the dark for 20 min. Lysates were digested with LysC (Wako) or trypsin (Promega) at a 1:100 (enzyme:substrate) ratio for 2 hrs at RT. pH of the lysates were adjusted to 8.5 and the lysates were incubated with m-aminophenylborinic acid agarose for 1 hr at RT. Beads were washed with the SDS wash buffer (1% SDS, 100 mM HEPES pH 8.5, 150 mM NaCl) for three times, and then the wash buffer (100 mM HEPES pH 8.5, 150 mM NaCl) for five times. Beads were incubated with 0.5 M $NH_2OH$ overnight. Released peptides were desalted on Sep-Pak C18 columns (Waters) according to manufacturer's instructions.

Mass spectrometry analysis and data processing: Samples were analyzed by LC-MS/MS on an LTQ-Velos Pro Orbitrap mass spectrometer (Thermo Fischer Scientific, San Jose, Calif.) using a top twenty method[23]. MS/MS spectra were searched against a composite database of the human IPI protein database and its reversed complement using the Sequest algorithm. Search parameters allowed for a static modification of 57.02146 Da for Cys and a dynamic modification of addition of 15.0109 Da to Asp and Glu, and, when applicable, the stable isotope (10.00827 Da) and (8.01420 Da) on Arg and Lys, respectively. Search results were filtered to include <1% matches to the reverse data base by the linear discriminator function using parameters including Xcorr, dCN, missed cleavage, charge state (exclude 1+ peptides), mass accuracy, peptide length and fraction of ions matched to MS/MS spectra[24]. Localization of ADP-ribosylation sites was assessed by the ModScore algorithm based on the observation of site-specific fragment ions[25]. Sites with scores≥13 (p≤0.05) were considered localized. Peptide quantification was performed as previously described[23] and ADP-ribosylation motifs were extracted using the Motif-X algorithm using a significance threshold of P<0.001[26].

Mammalian lentiviral shRNAs: Generation of the lentiviruses was carried out as described previously[23]. Briefly, shRNA plasmids were co-transfected into HEK293TD cells along with packaging (Δ8.9) and envelope (VSVG) expression plasmids using lipofectamine 2000 (Invitrogen). Two days after transfection, viral supernatants were harvested and filtered. Recipient cells were infected in the presence of a serum-containing medium supplemented with 8 µg/ml polybrene. Following infection for 36 h, cells were treated with 2.0 µg/ml puromycin and cells that stably expressed the shRNAs were selected.

Boronate beads pull down analysis: DDX21 and GAR1 were cloned into a pKH3 vector. The GAR1 point mutant (Glu67Gln, Glu74Gln, Glu80Gln, Asp81Asn and Glu104Gln) was generated using the QuickChange site-directed mutagenesis kit (Stratagene). shPARG HEK293T cells were transfected with the corresponding constructs using Lipofectamine 2000 (Invitrogen). Isolation of poly-ADP-ribosylated proteins for immunoblotting analyses was performed as described[27] with modifications. Briefly, cells were lysed in SDS lysis buffer (1% SDS, 10 mM HEPES pH 7.0, 2 mM $MgCl_2$, 500 U Benzonase), which were then adjusted to pH 8.5. Lysates were mixed with m-aminophenyl-boronic acid-agarose. After one hour incubation at room temperature, beads were washed with the SDS wash buffer (1% SDS, 100 mM HEPES pH 8.5, 150 mM NaCl) and subsequently with the wash buffer (100 mM HEPES pH 8.5, 150 mM NaCl). Beads were mixed with 3M ammonium acetate, pH 5.0 for 1.5 hours, and washed once with the SDS lysis buffer. Proteins were eluted by incubating the beads with 4×SDS-PAGE sample loading buffer at 95° C. for 10 min and were subjected to immunoblotting analyses.

Immunoblotting analysis: Samples were subjected to electrophoresis using the standard SDS-PAGE method. Proteins were transferred to a nitrocellulose membrane (Whatman). Membranes were blocked with a TBST buffer (25 mM Tris-HCl, pH 7.5, 150 mM NaCl, 0.05% Tween 20) containing 3% nonfat dried milk, and probed overnight with primary antibodies at 4° C. and for 1 h at RT with peroxidase-conjugated secondary antibodies. Blots were developed using enhanced chemiluminescence, exposed on autoradiograph film and developed using standard methods.

Calculation of the relative solvent-accessible area: Twenty five structure files were found in the Protein Data Bank (PDB) that corresponded to proteins that contained multiple ADP-ribosylation sites, including LIG3 (1UW0, 11MO), EWB (2CPE), PCNA(1VYM), FBL(2IPX), FEN1(3q8k), SERPINC1(2B4X), H2AFY(3IID), UBC(laar), NCL(2FC9), GAPDH(1U8F), LDHB(1T2F), H2AFY2(2XD7), FUS (2LA6), THOC4(3ULH), TOP1(1A31), PARP1(2L30, 2L31, 2RIQ, 2COK, 2CR9), UHRF1(3CLZ), MKI67(1R21), UBTF(1K99), YY1(1UBD). Singly modified proteins were not included in order to minimize the bias introduced by unidentified ADP-ribosylation sites in the proteins. Unambiguously localized ADP-ribosylated Glu residues (a total of 59 sites) were mapped onto the structures and the relative solvent-accessible side-chain area for ADP-ribosylated and unmodified-Glu residues in these structures was calculated using NACCESS[28] with a default probe size of 1.4 Å.

REFERENCES

1. Chambon, P., Weill, J. D. & Mandel, P. *Biochem. Biophys. Res. Commun.* 11, 39-43 (1963).
2. D'Amours, D., Desnoyers, S., D'Silva, I. & Poirier, G. G. *Biochem. J.* 342, 249-268 (1999).
3. Masson, M. et al. *Mol. Cell Biol.* 18, 3563-3571 (1998).
4. Wahlberg, E. et al. *Nat Biotechnol* 30, 283-288 (2012).
5. Durkacz, B. W., Omidiji, O., Gray, D. A. & Shall, S. *Nature* 283, 593-596 (1980).
6. Rouleau, M., Patel, A., Hendzel, M. J., Kaufmann, S. H. & Poirier, G. G. *Nat. Rev. Cancer.* 10, 293-301 (2010).
7. Farmer, H. et al. *Nature* 434, 917-921 (2005).
8. Tulin, A. *Nat. Biotechnol.* 29, 1078-1079 (2011).
9. Gagne, J. P. et al. *Nucleic Acids Res.* 36, 6959-6976 (2008).
10. Dania, N. et al. *Proc. Natl. Acad. Sci. U.S.A.* 106, 4243-4248 (2009).
11. Hengel, S. M. & Goodlett, D. R. *International journal of mass spectrometry* 312, 114-121 (2012).
12. Matic, I., Ahel, I. & Hay, R. T. *Nat Methods* 9, 771-772 (2012).
13. Tao, Z., Gao, P. & Liu, H. W. *J. Am. Chem. Soc.* 131, 14258-14260 (2009).
14. Hassa, P. O., Haenni, S. S., Elser, M. & Hottiger, M. O. *Microbiology and molecular biology reviews: MMBR* 70, 789-829 (2006).
15. Liu, X. C. & Scouten, W. H. *Methods Mol. Biol.* 147, 119-128 (2000).
16. Moss, J., Yost, D. A. & Stanley, S. J. *J. Biol. Chem.* 258, 6466-6470 (1983).
17. Loseva, O. et al. *J. Biol. Chem.* 285, 8054-8060 (2010).
18. Chapman, J. D., Gagne, J. P., Poirier, G. G. & Goodlett, D. R. *Journal of proteome research* (2013).
19. Ali, A. A. et al. *Nat Struct Mol Biol* 19, 685-692 (2012).
20 Zhang, Y. et al. *Nat Cell Biol* 13, 623-629 (2011).
21. Liu, X. et al. *Clinical cancer research: an official journal of the American Association for Cancer Research* 18, 510-523 (2012).
22. Patel, A. G., De Lorenzo, S. B., Flatten, K. S., Poirier, G. G. & Kaufmann, S. H. *Clinical cancer research: an official journal of the American Association for Cancer Research* 18, 1655-1662 (2012).
23. Yu, Y. et al. *Science* 332, 1322-1326 (2011).
24. Huttlin, E. L. et al. *Cell* 143, 1174-1189 (2010).
25. Kim, W. et al. *Mol. Cell* 44, 325-340 (2011).
26. Schwartz, D. & Gygi, S. P. *Nat. Biotechnol.* 23, 1391-1398 (2005).
27. Oei, S. L. & Shi, Y. *Biochem Biophys Res Commun* 285, 27-31 (2001).
28. Hubbard, S. J., Campbell, S. F. & Thornton, J. M. *J. Mol. Biol.* 220, 507-530 (1991).
29. Langelier, M. F., Planck, J. L., Roy, S. & Pascal, J. M. *Science* 336, 728-732 (2012).

SUPPLEMENTARY TEXT

Hydroxylamine Does Not React Nonspecifically with Free Asp and Glu Residues

We incubated crude Lys-C digests of shPARG HEK293T cells with 0.5 M $NH_2OH$ in 200 mM HEPES (pH 8.5). We prepared a negative control sample, where we excluded $NH_2OH$ from the mixture, and a positive control sample, where we induced ADP-ribosylation in shPARG HEK293T cells using $H_2O_2$ treatment, performed Lys-C digest, boronate beads binding, and then $NH_2OH$ elution. We acquired LC-MS/MS data for these three samples and performed database searches using +15.0109 Da on Asp/Glu as a variable modification. We filtered down the final dataset to contain a 1% false discovery rate.

We identified a very similar total number of peptides (9447 vs. 9431) between the negative control sample and the sample incubated with $NH_2OH$. We also identified a very similar number of Asp/Glu modified (+15.0109 Da) peptides between these two samples (68 vs 74). However, the number of reverse Asp/Glu modified peptides (31 and 32) suggested that most of these modified peptides were from spectra of low quality and were likely incorrect identifications. In contrast, the 2236 peptides identified in the positive control sample contained 845 Asp/Glu-modified peptides (with only 8 reverse hits). These results confirmed that $NH_2OH$ does not cause unwanted side reactions with free Asp/Glu residues.

We also found a substantial overlap of Asp/Glu-ADP-ribosylated proteins between shPARG HCT116 and shPARG HEK293T cells, indicating that DNA damage induces Asp/Glu-ADP-ribosylation of a core set of proteins in different cell types.

Boronate Affinity Chromatography Combined with $NH_2OH$ Elution Offers an Integrated Strategy for Site-Determination of Asp/Glu-ADP-Ribosylation Several investigators have used boronate affinity chromatography to isolate ADP-ribosylated peptides, and used ETD (electron transfer dissociation) to preserve ADP-ribose for sequence-specific analysis of this modification. However, fragmentation of the pyrophosphate bond still occurs, and these studies have so far been limited to model peptides and proteins[1,2]. Our large-scale approach offers several unique advantages. Because the hydroxamic derivative of Asp/Glu is stable, our approach can be applied on any mass spectrometers with conventional CID capabilities. Each ADP-ribose contains two negative charges, creating an insurmountable barrier for ionization of PARylated peptides in positive ion mode. Again by performing the $NH_2OH$-mediated amide-exchange reaction, we removed these highly acidic chains to eliminate the ionization issue, while preserving the site information. This small tag (Δ=+15.0109 Da) is expected not to interfere with ionization of the peptides, yielding an ideal situation for analyses of these peptides by liquid chromatography-electrospray ionization mass spectrometry (LC-ESI-MS). Finally, we bind the digests of crude cell extracts to boronate beads, remove the nonspecifically bound peptides, and then elute the ADP-ribosylated peptides by $NH_2OH$ treatment. This elution condition does not affect the binding of ADP-ribose to the boronate beads, but instead only releases the derivatized peptides. It is important to note that the results of our approach are not affected by the chain length or the topology of PAR.

Our integrated approach provides remarkable sensitivity for site-determination of Asp/Glu-ADP-ribosylation under various experimental conditions. For example, we were able to identify a total of 115 Asp/Glu-ADP-ribosylated peptides from 25 proteins in control (shGFP) HCT116 cells in response to oxidative DNA damage. Many of these proteins were also identified in the shPARG HCT116 cells. The lower number of identified peptides/proteins in shGFP HCT116 cells is not surprising because once formed, poly-ADP-ribose is rapidly degraded in vivo by PARG and ADP-ribosylated proteins are therefore of low abundance in cells with normal levels of PARG[3]. We also asked whether the ADP-ribosylated proteome will respond differently to another DNA-damaging agent, MNNG. We identified 11 and 112 Asp/Glu-ADP-ribosylated proteins from shGFP and shPARG HCT116 cells, respectively, in response to MNNG treatment. Many of the ADP-ribosylated proteins (65 out of 112) were also identified in $H_2O_2$-treated shPARG HCT116 cells, suggesting that different DNA damage mechanisms may induce a similar change in the Asp/Glu-ADP-ribosylated proteome. We finally investigated the proteins that were ADP-ribosylated under the basal conditions (shGFP HCT116 cells with no DNA damage). The only two modified proteins we identified were PARP1 and CASC3 (CASC3 has recently be shown to be a tankyrase substrate[4]).

Gene Ontology Analysis of the Asp/Glu-ADP-Ribosylated Proteins

We mapped the Asp/Glu-ADP-ribosylated proteins in PARG-depleted HCT116 cells to Gene Ontology (GO) terms with respect to Biological Process (BP) using the Database for Annotation, Visualization and Integrated Discovery (DAVID)[5]. The top enriched BPs included chromosome organization ($P=1.51\times10^{-15}$), transcription ($P=1.33\times10^{-13}$), DNA metabolic process ($P=1.03\times10^{-11}$) and DNA repair ($P=1.01\times10^{-10}$). We found that these proteins were enriched for domains including the RNA recognition motif, ATP-binding helicase and PHD-type zinc finger, and were mainly localized to the nuclear lumen and chromosome.

To gain further insight into the biological functions that could be regulated by protein PARylation, we mapped these Asp/Glu-ADP-ribosylated proteins to the Search Tool for the Retrieval of Interacting Genes/Proteins (STRING) database[6] to examine the physical and functional interaction among them. We found that these proteins had high network connectivity with several cellular functions forming tightly connected clusters containing known macromolecular complexes.

One of these functional networks was related to chromosome organization. We found that many SMC (structural maintenance of chromosomes) proteins were ADP-ribosylated, including SMC1A, SMC3, SMC4 and SMC6. The SMC proteins form complexes to regulate many aspects of the higher-order chromosome dynamics. For example, SMC1 and SMC3 are the core subunits of a complex that is involved in sister chromatid cohesion whereas SMC2 interacts with SMC4 to form the core of the condensin complex that is involved in chromosome condensation[7]. We infer that their interaction with the other SMC proteins and/or with DNA can be regulated by ADP-ribosylation. In addition, within this network, we identified 6 unequivocally assigned ADP-ribosylation sites on CTCF. CTCF is a chromatin insulator protein that binds to specific sequences located in imprinting control regions, creating a 3-dimensional loop structure that regulates allele-specific transcription by physically separating promoters from enhancers[8]. Using an in vitro PARylation assay, CTCF was previously shown to be PARylated in its N-terminus (amino acids 1-277)[9]. Indeed, the 6 ADP-ribosylation sites we identified were clustered within a small region of amino acids 161-242. It has been shown that only the PARylated form of CTCF is able to bind to imprinting control regions, and treatment of cells with a PARP inhibitor affects the insulator function of most CTCF target sites[9]. The ADP-ribosylation sites on SMC proteins and CTCF can be used to characterize PARylation in epigenetic regulation.

ADP-ribosylated proteins (including PARP1 itself) also forms a large protein network involved in the DNA repair process. We found three of the ADP-ribosylation sites (Asp119, Asp121 and Glu123) of PCNA were localized at the interface between PCNA and FEN1. In particular, PCNA Asp120 is 2.44 Å away from FEN1 Arg355, which can form a potential salt bridge, which may be disrupted by ADP-ribosylation.

We also found that proteins involved RNA splicing were extensively modified. In particular, many heterogeneous nuclear ribonucleoproteins (hnRNPs) were ADP-ribosylated, including hnRNPA0, hnRNPD, hnRNPR, hnRNPU, hnRNPUL1 and hnRNPL. The hnRNPs are RRM- and KH-domain containing RNA binding proteins, which have multiple roles in pre-mRNA and mRNA metabolism. Specifically, they bind to the exon and intron splicing silencers on pre-mRNAs and are a part of the H (heterogeneous) complex that regulates alternative splicing events[10]. Together with a recent study which shows that hnRNPs are a major class of PAR-binding proteins[11], these results indicate that ADP-ribosylation provides a mechanism for dynamic modulation of RNA splicing.

Mapping of the Asp/Glu-ADP-Ribosylated Residues onto the Structures of PARP1

We found that PARP1 was automodified with a total of 37 unambiguously assigned Asp/Glu-ADP-ribosylation sites (Glu75, Asp80, Glu89, Glu115, Glu129, Asp154, Glu167, Glu174, Glu189, Asp190, Glu211, Asp216, Glu217, Glu275, Asp306, Asp313, Glu359, Asp386, Glu447, Glu455, Asp456, Asp460, Glu470, Glu483, Glu487, Glu490, Glu512, Glu513, Glu539, Asp560, Glu575, Asp576, Asp577, Glu641, Asp643, Asp647, Glu649), including those previously reported, Glu189, Asp386, Glu455, Asp 460, Glu487, Glu490 and As577[12,13]. In fact, among the proteins that are modified, PARP1 has the largest number of ADP-ribosylation sites identified, correlating with the previous observation that a large fraction of cellular Poly-ADP-ribose is attached to PARP1 itself[14].

Although it is well established that PARP1 serves as a major sensor for DNA lesions, little is known about how binding to DNA strand breaks leads to its activation. Recently, Langelier et al. reported the structure of a DNA double-strand break in complex with human PARP-1 (Zn1, Zn3 and WGR-CAT domains)[15]. The structure suggests that PARP1 binds to DNA as a monomer. The binding triggers a conformational distortion of the catalytic domain, which potentially brings the BRCT domain (a domain traditionally believed to be the main auto-modification region) to proximity for auto-PARylation in cis. Structural and biochemical studies reported by Ali et al. indicate otherwise that PARP-1 likely binds to DNA as a dimer, which carries out trans-automodification[16]. We mapped the identified auto-modification residues onto the PARP1 structures and found that a large number of the sites resided outside of the BRCT domain. In particular, the distance between the catalytically important Gly862[17] and an ADP-ribosylated residue, Glu189, is more than 77 Å. Considering that the DNA/PARP1 complex already represents the activated state of the enzyme, our data indicate that the inter-molecule model explains PARP1 automodification.

Iniparib has a Negligible Effect on PARP1 Activity in Intact Cells

From an immunoblotting assay, we found that Iniparib treatment had little effect on PARP activity. Iniparib (the prodrug of 4-iodo-3-nitrosobenzamide), however, was originally developed as a covalent inhibitor of PARP1[18], which is different from the other NAD$^+$-competitive PARP inhibitors. It is possible that Iniparib might inhibit a subset of PARP substrates, which might explain its clinical efficacy in certain cases[19]. This hypothesis, however, cannot be easily tested using the antibody-based approaches, which only measure the gross level of cellular PARylation. Indeed, our mass spectrometric results showed that a peptide from the RNA helicase DDX21 decreased by about 4-fold upon Iniparib treatment (the same peptide decreased by more than 11-fold after 1 µM Olaparib treatment). However, since 50 µM of Iniparib was used, and most of the peptides had a change in their ADP-ribosylation level of less than two fold, we conclude that Iniparib has a negligible effect on PARP activity in vivo (with a potency that is lower than the prototype PARP inhibitor 3-AB).

ADP-Ribosylated Glu Residues have High Solvent-Accessible Areas

We gathered from the Protein Data Bank (PDB) the 25 structural files available for the multiply ADP-ribosylated proteins identified in this study and mapped the unambiguously localized ADP-ribosylated Glu residues onto these structures. 52% of the modified Glu residues were highly solvent-exposed (relative solvent-accessible area of greater than 80%), which was dramatically higher than that (20%) of unmodified Glu residues. Overall, ADP-ribosylated Glu residues (median relative solvent-accessible area=81.5%) were significantly more exposed than unmodified Glu residues (median relative solvent-accessible area=60.7%) (P=5.4×10$^{-6}$, Wilcoxon test). On a primary sequence level, we found that many ADP-ribosylated Glu were in the vicinity of Pro residues. Pro is known to cause kinks to helices, and is frequently solvent-exposed[20]. These results thus indicate that local solvent accessibility provides a determinant of whether an Asp/Glu residue can be modified by ADP-ribosylation.

REFERENCES

1. Hengel, S. M., Shaffer, S. A., Nunn, B. L. & Goodlett, D. R. Tandem mass spectrometry investigation of ADP-ribosylated kemptide. *J Am Soc Mass Spectrom* 20, 477-483 (2009).
2. Rosenthal, F. et al. Identification of distinct amino acids as ADP-ribose acceptor sites by mass spectrometry. *Methods Mol Biol* 780, 57-66 (2011).
3. D'Amours, D., Desnoyers, S., D'Silva, I. & Poirier, G. G. Poly(ADP-ribosyl)ation reactions in the regulation of nuclear functions. *Biochem. J.* 342, 249-268 (1999).
4. Zhang, Y. et al. RNF146 is a poly(ADP-ribose)-directed E3 ligase that regulates axin degradation and Wnt signalling. *Nat Cell Biol* 13, 623-629 (2011).
5. Huang da, W., Sherman, B. T. & Lempicki, R. A. Bioinformatics enrichment tools: paths toward the comprehensive functional analysis of large gene lists. *Nucleic Acids Res.* 37, 1-13 (2009).
6. Szklarczyk, D. et al. The STRING database in 2011: functional interaction networks of proteins, globally integrated and scored. *Nucleic Acids Res* 39, D561-568 (2011).
7. Hirano, T. The ABCs of SMC proteins: two-armed ATPases for chromosome condensation, cohesion, and repair. *Genes Dev* 16, 399-414 (2002).
8. Caiafa, P., Guastafierro, T. & Zampieri, M. Epigenetics: poly(ADP-ribosyl)ation of PARP-1 regulates genomic methylation patterns. *FASEB J* 23, 672-678 (2009).
9. Yu, W. et al. Poly(ADP-ribosyl)ation regulates CTCF-dependent chromatin insulation. *Nat Genet* 36, 1105-1110 (2004).
10. Matlin, A. J., Clark, F. & Smith, C. W. Understanding alternative splicing: towards a cellular code. *Nat Rev Mol Cell Biol* 6, 386-398 (2005).
11. Gagne, J. P., Hunter, J. M., Labrecque, B., Chabot, B. & Poirier, G. G. A proteomic approach to the identification of heterogeneous nuclear ribonucleoproteins as a new family of poly(ADP-ribose)-binding proteins. *Biochem J* 371, 331-340 (2003).
12. Chapman, J. D., Gagne, J. P., Poirier, G. G. & Goodlett, D. R. Mapping PARP-1 Auto-ADP-ribosylation Sites by Liquid Chromatography-Tandem Mass Spectrometry. *Journal of proteome research* (2013).
13. Tao, Z., Gao, P. & Liu, H. W. Identification of the ADP-ribosylation sites in the PARP-1 automodification domain: analysis and implications. *J. Am. Chem. Soc.* 131, 14258-14260 (2009).
14. Virag, L. & Szabo, C. The therapeutic potential of poly (ADP-ribose) polymerase inhibitors. *Pharmacol Rev* 54, 375-429 (2002).
15. Langelier, M. F., Planck, J. L., Roy, S. & Pascal, J. M. Structural basis for DNA damage-dependent poly(ADP-ribosyl)ation by human PARP-1. *Science* 336, 728-732 (2012).
16. Ali, A. A. et al. The zinc-finger domains of PARP1 cooperate to recognize DNA strand breaks. *Nat Struct Mol Biol* 19, 685-692 (2012).
17. Gandhi, V. B. et al. Discovery and SAR of substituted 3-oxoisoindoline-4-carboxamides as potent inhibitors of poly(ADP-ribose) polymerase (PARP) for the treatment of cancer. *Bioorganic & medicinal chemistry letters* 20, 1023-1026 (2010).
18. Mendeleyev, J., Kirsten, E., Hakam, A., Buki, K. G. & Kun, E. Potential chemotherapeutic activity of 4-iodo-3-nitrobenzamide. Metabolic reduction to the 3-nitroso derivative and induction of cell death in tumor cells in culture. *Biochem Pharmacol* 50, 705-714 (1995).
19. Fogelman, D. R. et al. Evidence for the efficacy of Iniparib, a PARP-1 inhibitor, in BRCA2-associated pancreatic cancer. *Anticancer Res* 31, 1417-1420 (2011).
20. Woolfson, D. N. & Williams, D. H. The influence of proline residues on alpha-helical structure. *FEBS Lett* 277, 185-188 (1990).
21. Rouleau, M., Patel, A., Hendzel, M. J., Kaufmann, S H & Poirier, G. G. PARP inhibition: PARP1 and beyond. *Nat. Rev. Cancer.* 10, 293-301 (2010).
22. Wahlberg, E. et al. Family-wide chemical profiling and structural analysis of PARP and tankyrase inhibitors. *Nat Biotechnol* 30, 283-288 (2012).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:
1. A method for labeling sites of poly-ADP-ribosylation (PARylation) comprising steps:

(a) enriching for PARylated proteins comprising treating cell lysates comprising PARylated proteins and DNA/RNA with an endonuclease that cleaves the DNA/RNA but not the PAR; and separating the PARylated proteins from the cleaved DNA/RNA;

(b) binding the PARylated proteins to a PAR-affinity substrate; and (c) labeling the PARylation sites comprising eluting the PARylated proteins from the PAR-affinity substrate with a nucleophilic amine exchange reactant, wherein the reactant labels PARylation sites of the proteins.

2. The method of claim 1 further comprising: repeating the steps in the presence and absence of an inhibitor of ADP-ribosylation, and detecting changes in protein ADP-ribosylation as a result of the inhibitor.

3. The method of claim 1 further comprising stable isotope labeling by amino acids in cell culture (SILAC).

4. The method of claim 1 wherein a PARP1 Asp/Glu-ADP-ribosylation site is labeled and detected, the site selected from: Glu75, Asp80, Glu89, Glu115, Glu129, Asp154, Glu167, Glu174, Asp190, Glu211, Asp216, Glu217, Glu275, Asp306, Asp313, Glu359, Glu447, Asp456, Glu470, Glu483, Glu512, Glu513, Glu539, Asp560, Glu575, Asp576, Glu641, Asp643, Asp647 and Glu649.

5. The method of claim 1 wherein the endonuclease is promiscuous, degrading both DNA and RNA, including single-stranded, double-stranded, circular or supercoiled, wherein upon digestion, all free nucleic acids present in solution are reduced to short (3-8 bases) 5'-monophosphate-terminated oligonucleotides.

6. The method of claim 1 wherein the endonuclease is of *Serratia marcescens*, including a genetically engineered form thereof.

7. The method of claim 1 wherein the affinity substrate preferentially binds PAR over forms of DNA and RNA, and is selected from a boronate substrate and a PAR-specific antibody substrate.

8. The method of claim 1 wherein the affinity substrate preferentially binds PAR over forms of DNA and RNA, and is selected from a boronate substrate and a PAR-specific antibody substrate, and is a solid phase selected from a resin bead based column, flow cell and surface.

9. The method of claim 1 wherein a reaction of a reactant and an ester of a Glu/Asp residue of the proteins generates an amide derivative of the Glu/Asp.

10. The method of claim 1 wherein a reaction of a reactant and an ester of a Glu/Asp residue of the proteins generates an amide derivative of the Glu/Asp, wherein the reactant is a nucleophilic amine exchange reactant compatible with the method.

11. The method of claim 1 wherein a reaction of a reactant and an ester of a Glu/Asp residue of the proteins generates an amide derivative of the Glu/Asp, wherein the reactant is hydroxylamine or hydrazine.

12. The method of claim 1 wherein:
the endonuclease is of *Serratia marcescens*, including a genetically engineered form thereof, and
the affinity substrate preferentially binds PAR over forms of DNA and RNA, and is selected from a boronate substrate and a PAR-specific antibody substrate.

13. The method of claim 1 wherein:
the endonuclease is of *Serratia marcescens*, including a genetically engineered form thereof,
the affinity substrate preferentially binds PAR over forms of DNA and RNA, and is selected from a boronate substrate and a PAR-specific antibody substrate, and is a solid phase selected from a resin bead based column, flow cell and surface.

14. The method of claim 1 wherein:
the endonuclease is of *Serratia marcescens*, including a genetically engineered form thereof, and
the affinity substrate preferentially binds PAR over forms of DNA and RNA, and is selected from a boronate substrate and a PAR-specific antibody substrate, and is a solid phase selected from a resin bead based column, flow cell and surface.

15. The method of claim 1 wherein:
the endonuclease is of *Serratia marcescens*, including a genetically engineered form thereof,
the affinity substrate preferentially binds PAR over forms of DNA and RNA, and is selected from a boronate substrate and a PAR-specific antibody substrate, and is a solid phase selected from a resin bead based column, flow cell and surface,
and
a reaction of a reactant and an ester of a Glu/Asp residue of the proteins generates an amide derivative of the Glu/Asp, wherein the reactant is hydroxylamine or hydrazine.

16. The method of claim 1 further comprising the step of detecting one or more of the PARylation sites.

17. The method of claim 1 further comprising generating an antibody against one or more of the PARylation sites.

18. The method of claim 1 further comprising generating an antibody against one or more of the PARylation sites using the labeled PARylation site(s) as an antigen or immunogen.

* * * * *